United States Patent [19]

Quinn

[11] 4,113,297
[45] Sep. 12, 1978

[54] DEVICE FOR INSERTING AND REMOVING CONTACT LENS

[76] Inventor: Jack Edward Quinn, 32724 Coastsite Dr., Rancho Palos Verdes, Calif. 90274

[21] Appl. No.: 858,436

[22] Filed: Dec. 7, 1977

[51] Int. Cl.² .............................................. A61F 9/00
[52] U.S. Cl. ................................................ 294/1 CA
[58] Field of Search ........... 294/1 CA, 1 R, 20, 64 R; 128/233, 249, 303 R; 206/5.1

[56] References Cited

U.S. PATENT DOCUMENTS

| 3,879,076 | 4/1975 | Barnett | 294/1 CA |
| 4,026,591 | 5/1977 | Cleaveland | 294/1 CA |

Primary Examiner—James B. Marbert
Attorney, Agent, or Firm—Edward A. Sokolski

[57] ABSTRACT

A shaft member is slidably mounted in a flotation chamber. Liquid is fed to the flotation chamber from a liquid storage chamber through a constricted tube when the storage chamber is squeezed, thereby slowly raising the liquid level in the flotation chamber. By virtue of the buoyancy provided by the liquid, the shaft is raised vertically within the flotation chamber as the storage chamber is squeezed and the flotation level in the flotation chamber raised. Means are provided on the end of the shaft for supporting a contact lens. An eye piece is mounted on the device around the end of the shaft, such that the user's eye can be placed on the eye piece and the contact lens raised into contact with the eyeball in its installed position. The eye piece used for inserting the lens is removable and can be replaced with an eye cup which can be filled with liquid for use in removing the lens by bathing it out.

5 Claims, 4 Drawing Figures

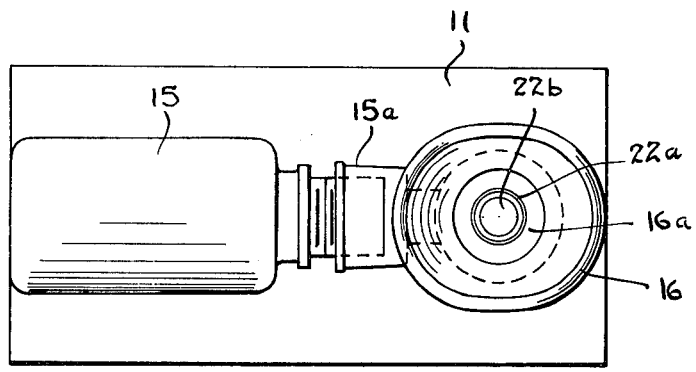
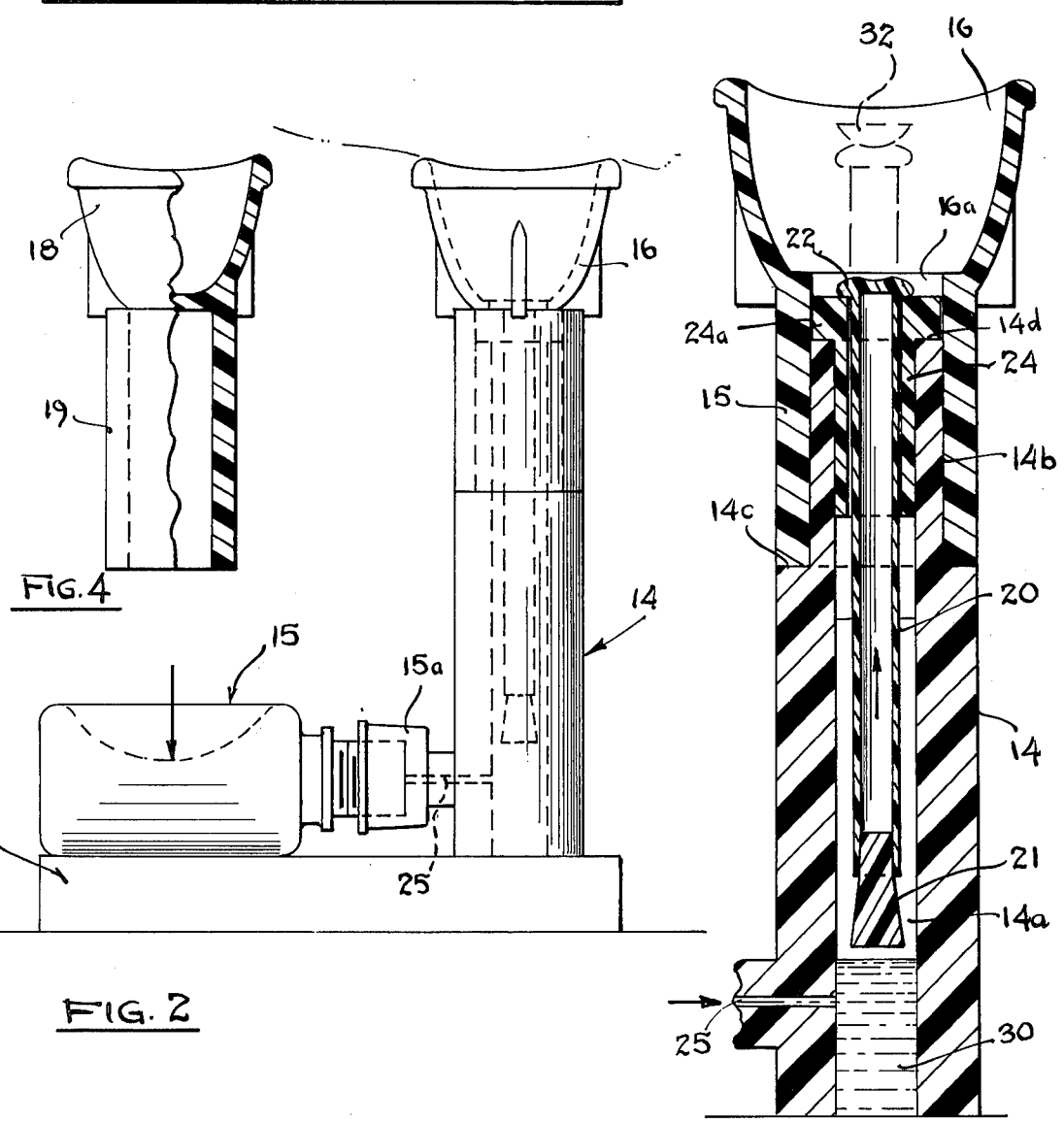
FIG. 1
FIG. 4
FIG. 2
FIG. 3

DEVICE FOR INSERTING AND REMOVING CONTACT LENS

This invention relates to a device for inserting and removing a contact lens, and more particularly to such a device which employs a rod for supporting the lens, which is raised to the eyeball in a flotation chamber.

The insertion or removal of contact lenses manually by persons having unsteady hands is difficult, if not impossible. Various devices have been developed for aiding in the insertion and removal of contact lenses, but none of these have been found to be as effective as would be desired for use by persons with unsteady hands. Thus, U.S. Pat. No. 3,934,914 to Carruthers, U.S. Pat. No. 3,922,025 to Updegraff, U.S. Pat. No. 3,129,971 to Kobler, and U.S. Pat. No. 3,791,689 to Boone, each shows a different hand held device in which the contact lens is held by suction while the device is positioned manually to place the contact lens on the user's eyeball. U.S. Pat. No. 3,304,113 to Hutchison, and U.S. Pat. No. 3,910,618 to Massenz, each shows a stand-held device in which an applicator for holding the contact lens is spring loaded and the eye is moved down into contact with the applicator. U.S. Pat. No. 3,600,028 to Henning describes a device for inserting and removing contact lenses which is mounted on a support stand and with which the user's eye is brought into contact with the applicator, whereupon an illuminating light is extinguished and the applicator is moved away from the user's eyeball.

The device of the present invention is an improvement over the aforementioned prior art devices in that it only requires of the user that he place his eye in position over a stand-supported eye piece and apply squeezing pressure to a liquid storage chamber supported on the stand to cause the lens to be inserted on the eye. To avoid the possibility of injury to the eye and to facilitate control of the movement of the positioning device, this positioning device is in the form of a rod member which is placed in a flotation chamber, the upward movement of the rod towards the eye being effected by raising the flotation level of the liquid in the flotation chamber. This change of flotation level in response to squeezing pressure of the operator is made very gradual by virtue of a constricted metering tube which interconnects the flotation chamber and the liquid storage chamber. The flotation member has a relatively small volume so that its buoyancy is limited, such that it will offer little resistance to inadvertent movement of the eyeball thereagainst. The device of the invention is of relatively simple and inexpensive construction which can be counted on for reliable operation over long periods of use, and is very simple and easy to operate even in the case of persons having very unsteady hands.

It is therefore an object of this invention to provide an improved device for inserting and removing contact lenses which is particularly suitable for persons having unsteady hands.

It is a further object of this invention to provide a simple device of highly economical construction for use in inserting and removing contact lenses.

Other objects of this invention will become apparent as the description proceeds in connection with the accompanying drawings, of which:

FIG. 1 is a top plan view of a preferred embodiment of the invention;

FIG. 2 is a side elevational view of the preferred embodiment;

FIG. 3 is a cross-sectional view illustrating the flotation chamber and applicator rod of the preferred embodiment; and FIG. 4 is a side elevational view of an eye cup assembly that can be used in the preferred embodiment for removing a contact lens.

Briefly described, the device of my invention is as follows:

A flotation chamber in the form of a vertical column and a liquid storage chamber are mounted on a stand. The storage chamber and the flotation chamber are interconnected by means of a constricted tube. The liquid storage chamber has flexible walls such that when these walls are squeezed, liquid is forced through the constricted tube into the flotation chamber, raising the level of the liquid therein in accordance with the squeeze pressure applied to the storage chamber. A rod member is placed in the flotation chamber, with freedom for vertical motion therein such that as the liquid level in the flotation chamber is raised, the rod will be floated in the liquid and will rise as the level of the liquid rises. Thus, as the liquid storage chamber walls are squeezed, one end of the rod slowly rises out from the top of the flotation chamber to a vertical position which can be controlled in accordance with the squeezing pressure applied to the liquid storage chamber. An eye piece having an aperture in the bottom thereof is mounted on the top portion of the flotation chamber to permit the user of the device to position his eye above the rod. The contact lens is placed on a cap member on the top of the rod and with the eye in position on the eye piece above the rod, the storage chamber walls are squeezed to bring the contact lens into proper position against the eyeball. The apertured eye piece used for inserting the contact lens can be replaced with an eye cup filled with water which can be used to remove the lens.

Referring now to the drawings, a preferred embodiment of the invention is illustrated. Rectangular block 11 forms a stand on which flotation chamber 14 and liquid storage chamber 15 are supported. Flotation chamber 14 may be in the form of a tube which is cemented and/or bolted to stand 11, with a cylindrical chamber 14a being formed in the center thereof. Flotation chamber 14 and stand 11 may be fabricated of a suitable hard plastic material. The top wall portion 14b of the chamber is undercut providing a ledge 14c. Slidably supported over undercut portion 14b and resting on ledge 14c is a cylindrical support member 15 which may be integrally formed with eye piece 16, or may be joined to the eye piece to form a two-piece assembly. It is to be noted that the eye piece assembly and its support are supported on chamber 14 for ready removal therefrom so that it can be replaced with eye cup 18 and its associated support 19, shown in FIG. 4, this second assembly being utilized in removing a contact lens.

Eye piece 16 has an aperture 16a formed in the bottom thereof to permit the passage of rod member 20 upward to the user's eye, as shown by the dashed outline of rod 20 in FIG. 3. Rod 20 may be hollow, as shown in FIG. 3, and sealed on the bottom end by means of a plug 21 and on the top end by means of a cap 22. Cap 22 is formed from a ring member 22a which forms the outer periphery thereof, and a dome shaped central portion 22b. It is to be noted that rod member 20 can be solid in lieu of being tubular, as shown for the preferred embodiment. Rod member 20 is slidably supported in sleeve member 24 which has a top circular lip portion 24a which rests on the top edge 14d of chamber 14. It is to be noted that rod member 20 is loosely fitted within sleeve 24 so as to permit access of the ambient air to the interior 14a of the chamber.

The interior of liquid storage chamber 15 is joined to the interior of flotation chamber 14 by means of a constricted tubular passageway 25 formed in the cap 15a of chamber 15, and the wall of chamber 14.

With rod 20 in its initial at-rest position, as shown in FIG. 3, the level of the liquid 30 within chamber 14 should be beneath the bottom-most portion of rod 20 with the rod in its lowermost position. In the use of the device, a contact lens is placed on cap 22 with the center of the lens resting on dome shaped portion 22b (as shown in the dashed illustration of FIG. 3). Liquid storage chamber 15 has walls which are flexible and when these walls are squeezed, as indicated by the dashed line in FIG. 2, liquid is forced from chamber 15 through passageway 25 into chamber 14. With increased pressure, the level of the liquid 30 within chamber 14 will gradually be raised until it reaches the level at which the rod will commence floating in the liquid. Then, as the liquid level is raised still further, rod 20 will be raised in accordance with its flotation level. Thus, the contact lens 32 placed on cap 22 will be raised upwardly until it comes into contact with the user's eye which is positioned along the edges of eye piece 16.

In view of the fact that the device is not held in one's hand but rather rests on stand 11, which is supported on a suitable table, the fact that one has an unsteady hand does not detract from the ability to insert the lens, as the hands need only by used to squeeze the walls of chamber 15 and not to position the lens. It is further to be noted that due to the fact that rod member 20 is driven upwardly purely by virtue of its flotation in the liquid contained within chamber 14, it exerts minimal upward pressure and offers little resistance to downward pressure so as to minimize the likelihood of injury to the eye during or after insertion of the contact lens.

The contact lens may be just as easily removed by placing eye cup 18 and its support 19 (shown in FIG. 4) in the same position occupied by eye piece 16 and support 15 in FIGS. 1-3. With eye cup 18 filled with water, the lid of the eye is held open and the eye is lowered into the water. Upon rotation of the eye under the water, the lens will readily float out from the eye into the cup.

While the invention has been described and illustrated in detail, it is to be clearly understood that this is intended by way of illustration and example only and is not to be taken by way of limitation, the spirit and scope of this invention being limited only by the terms of the following claims.

I claim:

1. A device for inserting and removing contact lenses comprising:
    a liquid flotation chamber having a longitudinal compartment formed therein,
    means for supporting said chamber with said compartment along an axis having a generally vertical orientation, a rod member slidably mounted in said compartment for motion along an axis substantially parallel to the longitudinal axis of said compartment,
    means for positioning a human eye in a predetermined position directly above said flotation chamber,
    a liquid storage chamber having fluid contained therein, and
    means for providing fluid communications between said chambers,
    whereby when fluid is transferred from said liquid storage chamber to said flotation chamber to raise the level of liquid within said flotation chamber, said rod member is raised towards the eye to bring the contact lens placed on said rod into contact therewith.

2. The device of claim 1 wherein the storage chamber is a container having flexible walls adapted to be manually squeezed to transfer the liquid from the storage chamber to the flotation chamber.

3. The device of claim 1 wherein said means for providing fluid communications between said chambers comprises a constricted passageway which limits the flow rate of liquid between said chambers.

4. The device of claim 1 wherein the eye positioning means comprises an eye piece member removably supported on the top portion of said chamber.

5. The device of claim 4 and further including an eye cup and support member adapted to replace said eye piece member for use in removing a lens.

* * * * *